US006740054B2

(12) United States Patent  
Stearns

(10) Patent No.: US 6,740,054 B2
(45) Date of Patent: May 25, 2004

(54) ORTHOPAEDIC BRACE ASSEMBLY

(75) Inventor: Jeffrey Stearns, Hopatcong, NJ (US)

(73) Assignee: EBI, L.P., Parsippany, NJ (US)

( * ) Notice: Subject to any disclaimer, the term of this patent is extended or adjusted under 35 U.S.C. 154(b) by 0 days.

(21) Appl. No.: 09/863,830

(22) Filed: May 23, 2001

(65) Prior Publication Data

US 2002/0013544 A1 Jan. 31, 2002

Related U.S. Application Data

(60) Provisional application No. 60/206,423, filed on May 23, 2000.

(51) Int. Cl.[7] .................................................. A61F 5/00
(52) U.S. Cl. ................................. 602/16; 602/26; 602/5
(58) Field of Search ............................... 602/5, 16, 26; 128/882

(56) References Cited

U.S. PATENT DOCUMENTS

| 4,361,142 A | * | 11/1982 | Lewis et al. .................. 602/16 |
| 4,732,143 A | * | 3/1988 | Kausek et al. ................. 602/16 |
| 4,790,299 A | * | 12/1988 | Marquette ..................... 602/26 |
| 4,940,045 A | * | 7/1990 | Cromartie ..................... 602/16 |
| 5,038,765 A | * | 8/1991 | Young et al. .................. 602/16 |
| 5,042,464 A | | 8/1991 | Skwor et al. ............. 128/80 C |
| 5,658,243 A | * | 8/1997 | Miller et al. ................... 602/26 |
| 5,658,244 A | * | 8/1997 | Townsend et al. ............. 602/26 |
| 5,672,152 A | * | 9/1997 | Mason et al. .................. 602/26 |
| 5,743,865 A | | 4/1998 | Townsend ..................... 602/26 |
| 5,857,989 A | * | 1/1999 | Smith, III ..................... 602/26 |
| 6,066,110 A | * | 5/2000 | Nauert ......................... 602/16 |

* cited by examiner

Primary Examiner—Michael A. Brown
Assistant Examiner—Fenn C Mathew
(74) Attorney, Agent, or Firm—Harness, Dickey & Pierce, P.L.C.

(57) ABSTRACT

An orthopaedic brace assembly includes a thigh cuff component, a calf cuff component and a pair of hinge assemblies. The thigh cuff component engages the wearer's leg above the knee and includes a suspension assembly having a pair of cantilevered arms. The calf cuff component engages the wearer's leg below the knee. The pair of hinge assemblies couples the thigh cuff component and the calf cuff component for relative articulation. The hinge assemblies include first and second arms interconnected for relative movement to one another through a range of articulation by first and second links. The hinge assemblies additionally include a series of stops which selectively snap fit to the first arm for limiting the range of articulation.

18 Claims, 7 Drawing Sheets

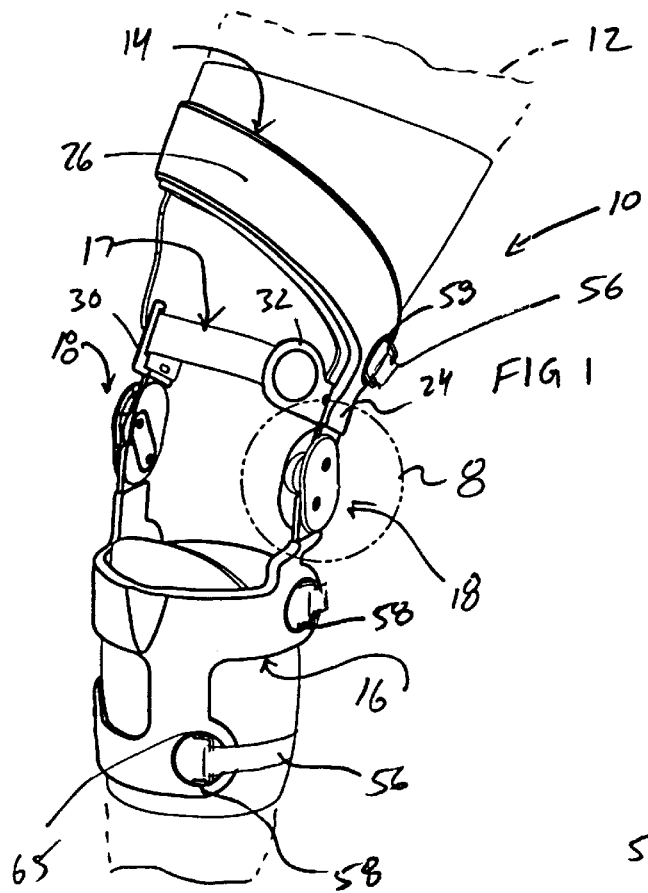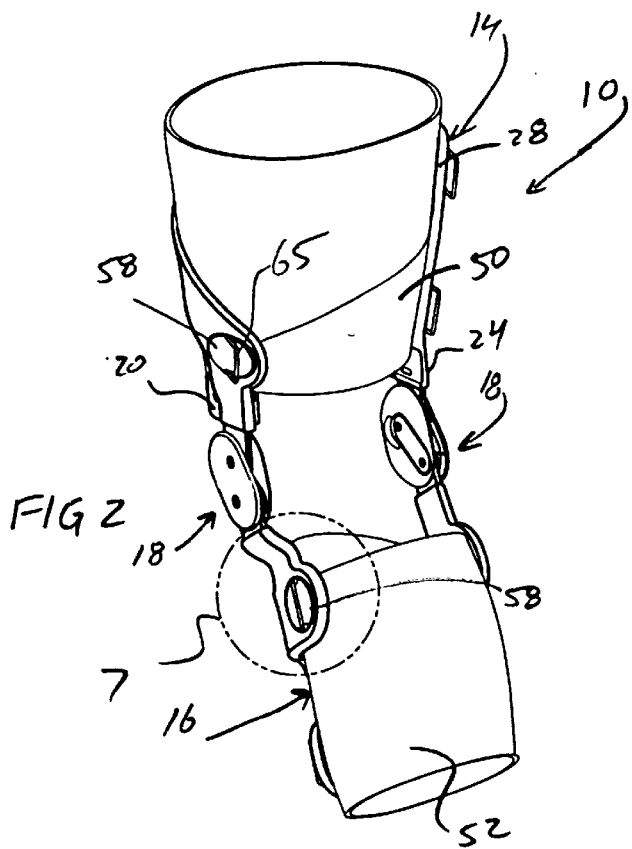

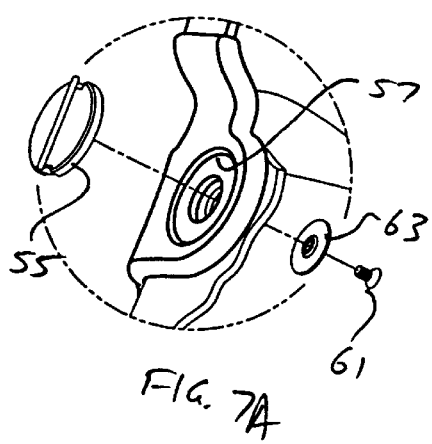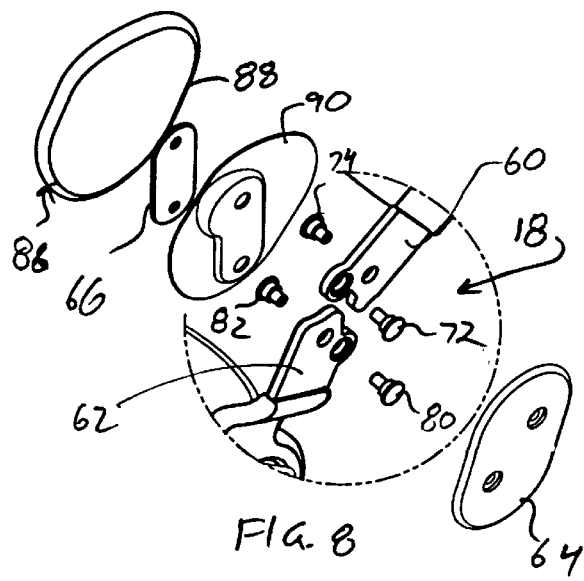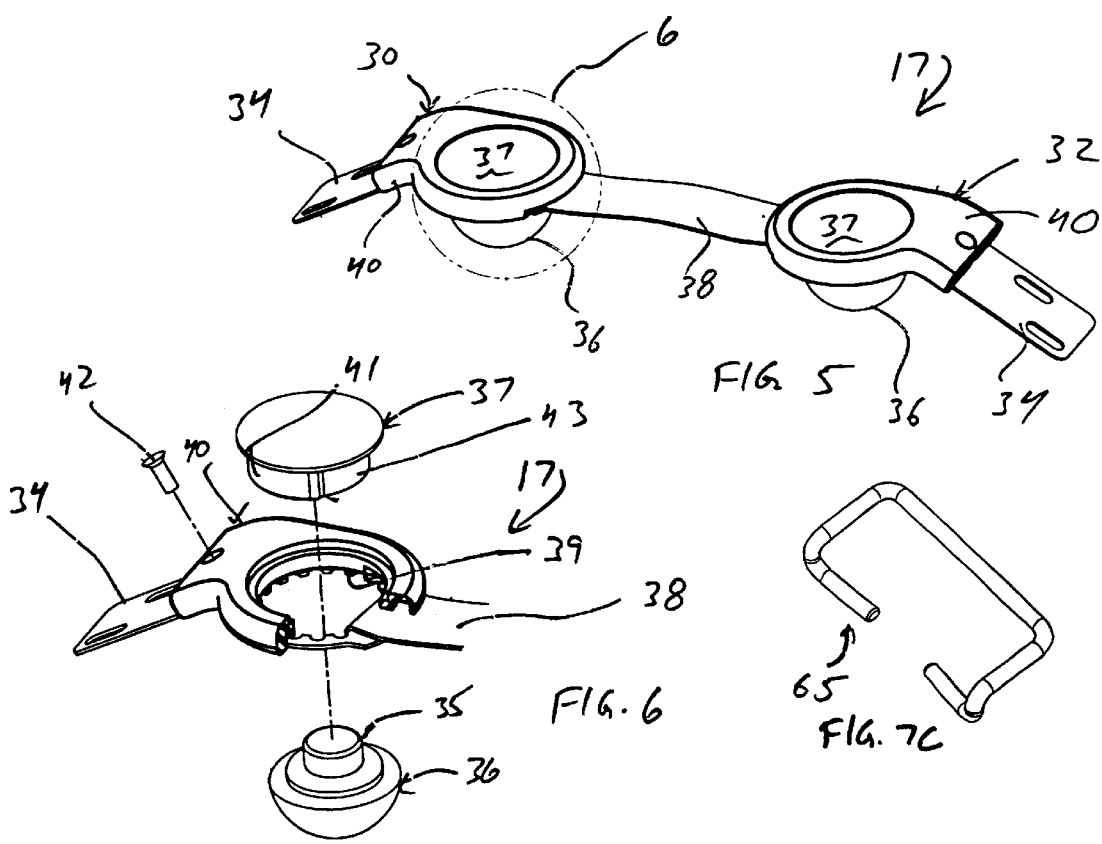

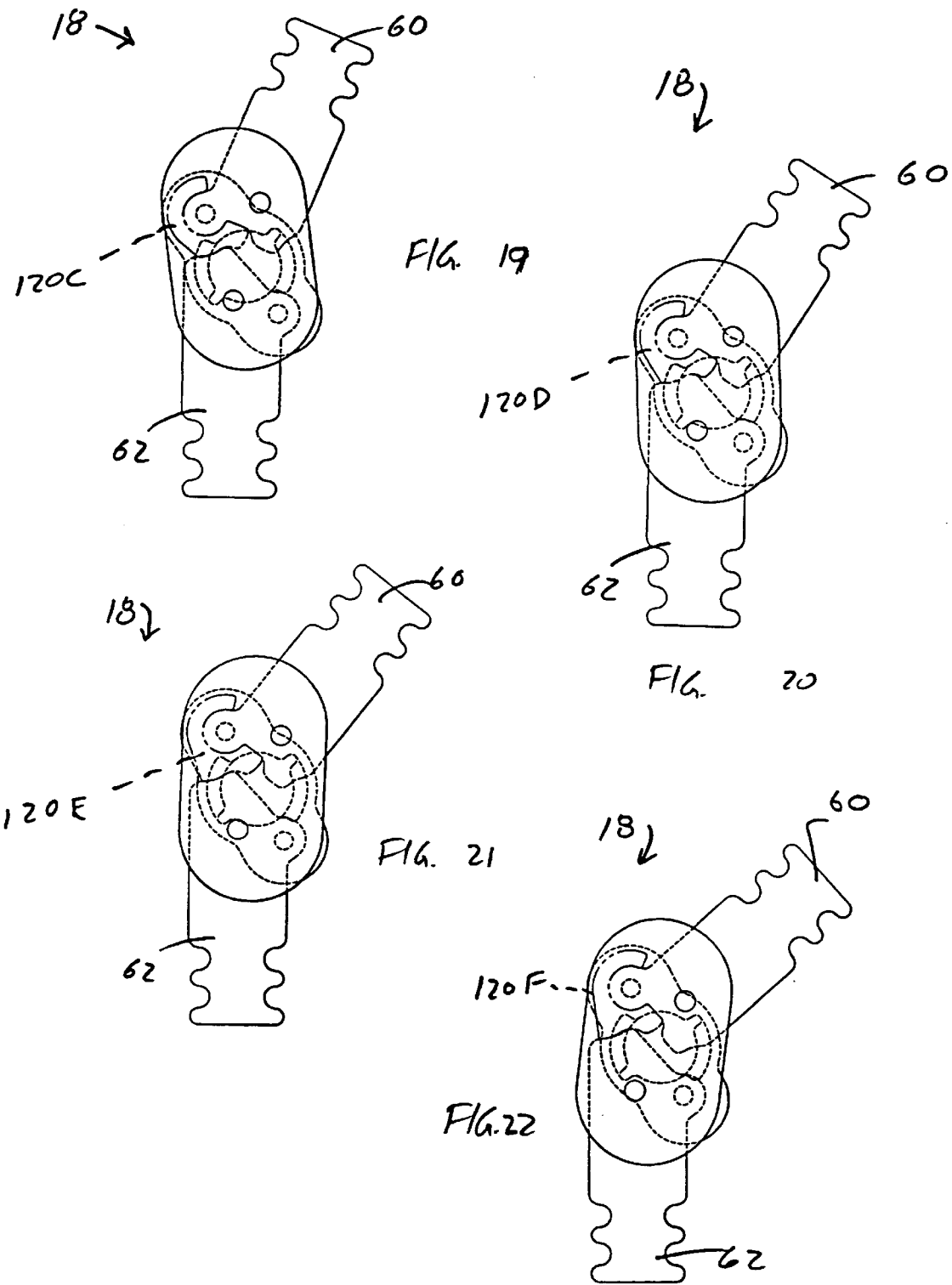

ORTHOPAEDIC BRACE ASSEMBLY

CROSS-REFERENCE TO RELATED APPLICATION

This application claims priority to a provisional application filed May 23, 2000 and assigned U.S. Ser. No. 60/206,423.

FIELD OF THE INVENTION

The present invention generally relates to orthopaedic braces. More specifically, the present invention is directed to an orthopaedic knee brace assembly and a hinge assembly therefor.

BACKGROUND OF THE INVENTION

Various devices are known for restricting the range of motion of a hinged joint to prevent injury and promote healing of a wearer's bone, joint or connective tissue. Such devices provide stabilization and support to the joint during a healing process. In addition, such devices can also be used to provide stabilization and support to an otherwise healthy joint.

It is often desired to limit the range of articulation of a hinged joint. For example, it is often desirable to limit the degree of extension of a knee joint during a period of rehabilitation. As the rehabilitation of the knee progresses, the knee joint typically becomes more flexible and can accommodate a greater range of extension.

One example of a prior known arrangement for limiting the range of articulation of a knee joint is shown and described in U.S. Pat. No. 4,715,363. This patent discloses upper and lower cuff members configured to accommodate a portion of the wearer's leg. The device is secured first with a pair of straps and subsequently with a pair of wide bands. U.S. Pat. No. 4,715,363 also discloses a set of pairs of wedges which selectively establish various maximum extension angles. The wedge pairs are secured to the hinges by threaded fasteners or screws.

Known devices for limiting the range of articulation of a hinged joint, including the device disclosed by U.S. Pat. No. 4,715,363, are all associated with disadvantages. For example, known devices do not allow a wearer to quickly and easily adjust a range of joint extension. Additionally, many known devices do not sufficiently and comfortably secure to a wearer's leg.

A need remains in the pertinent art for an improved orthopaedic brace assembly which addresses the disadvantages associated with prior known devices, including but not limited to those discussed above.

SUMMARY OF THE INVENTION

According to one aspect, the present invention relates to an orthopaedic brace assembly with improved fit and user comfort.

According to another aspect, the present invention relates to a hinge assembly for an orthopaedic brace which includes a plurality of removable stops for selectively adjusting a range of joint articulation.

In one form, the present invention provides, an orthopaedic brace assembly for constraining movement of a knee of a wearer's leg. The orthopaedic brace assembly includes a thigh cuff component, a calf cuff component and a pair of hinge assemblies. The thigh cuff component engages the wearer's leg above the knee and includes a suspension assembly having a pair of cantilevered arms. The calf cuff component engages the wearer's leg below the knee. The pair of hinge assemblies couples the thigh cuff component and the calf cuff component for relative articulation.

In another form, the present invention provides a hinge assembly for an orthopaedic brace including first and second arms and first and second links. The first link and second link interconnect the first and second arms for relative movement to one another through a range of articulation. The hinge assembly additionally includes a series of stops which selectively snap fit to the first arm for limiting the range of articulation.

BRIEF DESCRIPTION OF THE DRAWINGS

The present invention will become more fully understood from the detailed description and the accompanying drawings, wherein:

FIG. 1 is a front perspective view of an orthopaedic brace assembly constructed in accordance with the teachings of a preferred embodiment of the present invention, the orthopaedic brace assembly shown operatively attached to a human leg.

FIG. 2 is a rear perspective view of the orthopaedic brace assembly of the present invention shown removed from the leg.

FIG. 5 is an enlarged perspective view of a support assembly of the orthopaedic brace assembly of the present invention.

FIG. 6 is an exploded perspective view illustrating the detail of Circle 6 of FIG. 5.

FIG. 7A is an exploded perspective view illustrating the detail of Circle 7 of FIG. 2.

FIG. 7C is a perspective view of the hook proper of FIG. 7A.

FIG. 8 is an exploded perspective view illustrating the detail of Circle 8 of FIG. 1.

FIGS. 17–22 represent a series of front views of the hinge assembly of FIG. 9, each illustrated to include a different removable stop for establishing a maximum range of joint extension, each of the hinge assemblies articulated to the maximum extension position permitted by the particular stop.

DETAILED DESCRIPTION OF THE PREFERRED EMBODIMENTS

Figure 3:
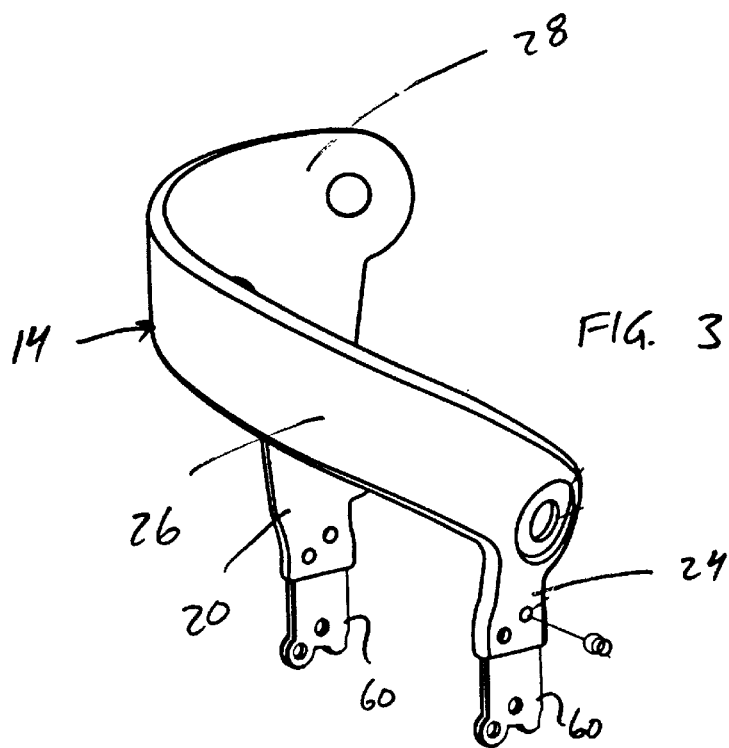
FIG. 3 is an enlarged perspective view of the thigh cuff component of the orthopaedic brace assembly of the present invention shown operatively associated with the upper arms of a pair of hinge assemblies.

The following description of the preferred embodiment of the present invention is merely exemplary in nature and is in no way intended to limit the subject invention or its application or uses.

With initial reference to FIGS. 1 and 2, an orthopaedic brace assembly constructed in accordance with the teachings of a preferred embodiment of the present invention is illustrated and generally identified at reference number 10. The orthopaedic brace assembly 10 is illustrated in the exemplary embodiment as a knee brace assembly and is shown in FIG. 1 operatively attached to a human leg 12 (shown in phantom). As shown, the knee brace assembly 10 is specifically constructed for a right leg 12. However, it will be appreciated by those skilled in the art that the teachings of the present invention are equally applicable for a left leg and also for other hinged joints.

With continued reference to FIGS. 1 and 2 and additional reference to FIGS. 3 through 11, the orthopaedic brace assembly 10 of the present invention will be further described. The orthopaedic brace assembly 10 is shown to generally include an upper cuff component or thigh cuff component 14, a lower cuff component or calf cuff component 16, a suspension assembly 17, and a pair of hinge assemblies 18. In the preferred embodiment, the thigh and calf cuff components 14 and 16 will be understood to be custom manufactured from a casting taken from a specific patient.

The thigh cuff component 14 is formed to fit the anterior portion of the wearer's leg above the knee. The thigh cuff component 14 includes two downwardly extending portions 20 and 24 positioned medially and laterally relative to the wearer's knee, respectively. A femoral transverse portion 26 of the thigh cuff component 14 is arcuately curved to conform to the wearer's thigh and includes a first end which intersects the downwardly extending portion 20 at an upper medial corner 28. The transverse member 26 transitions downwardly at an angle as it anteriorly circumscribes the wearer's thigh and intersects the downwardly extending portion 24. The thigh cuff component 14 is open at the posterior so that it may be placed over the user's leg 12 from the front.

With particular reference to FIGS. 1, 5 and 6, the thigh cuff component 14 is shown operatively associated with a suspension assembly 17. The suspension assembly 17 includes a pair of cantilevered suspension arms 30 and 32. The arms 30 and 32 engage the wearer's leg 12 above the knee. More specifically, the suspension arms 30 and 32 are positioned to engage the wearer's leg 12 superior to the condyles of the femur. In full knee flexion, the suspension arms 30 and 32 operate to control the tibia by providing translational and rotational stability otherwise provided by a normally functioning anterior cruciate ligament. The suspension arms 30 and 32 also function to prevent the brace assembly 10 from migrating during knee articulation. Each of the arms 30 and 32 is attached to one of the downwardly extending portions 20 and 24 through an angled bracket 34 (shown particularly in FIGS. 5 and 6). The angled brackets 34 inwardly orientate the arms 30 and 32 relative to the wearer's leg 12 at an angle of approximately 30°. In one particular application, each of the angled brackets 34 is secured to an associated one of the downwardly extending portions 20 and 24 with a pair of screws (not shown). Alternatively, the angled brackets 34 can be welded or otherwise fixedly attached.

Each of the arms 30 and 32 include a hemispherical cushioning member or dome member 36 attached to an inner side for directly engaging the wearer's leg 12. In the preferred embodiment, the cushioning members 36 are formed to include a stem 35 which is received by a base 37 and adhesively banded to the base 37. The base 37 is press-fit into an aperture 39 provided in the end of the associated angled bracket 34.

In the preferred embodiment, the arms 30 and 32 of the suspension assembly 17 are connected by a strap 38. The strap 38 is attached to each of the angled brackets 34 through capture between the angled bracket 34 and an injection molded suspension body 40. The suspension body 40 is secured to the associated angled bracket 34 through a rivet 42. An inwardly extending portion 41 of the bases 37 includes a reduced diameter portion 43 to accommodate the strap 38.

Figure 4:
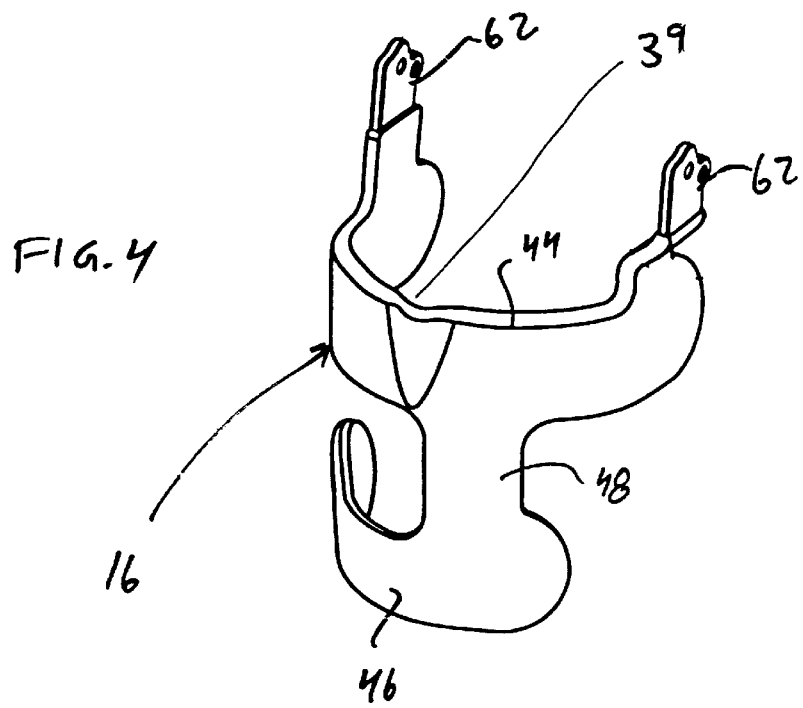
FIG. 4 is an enlarged perspective view of the calf cuff component of the orthopaedic brace assembly of the present invention shown operatively associated with the lower arms of a pair of hinge assemblies.
Figure 7B:
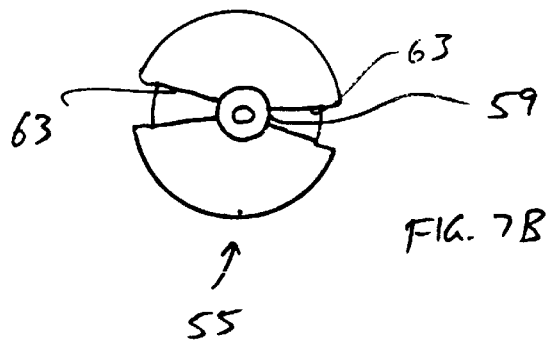
FIG. 7B is a rear view of the base of FIG. 7A.
Figure 12:
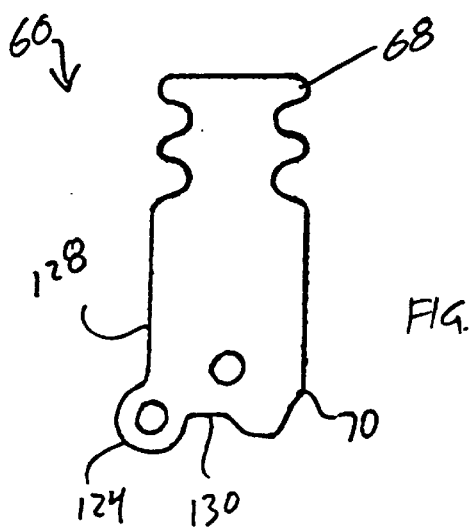
FIG. 12 is a front view of the upper arm of the hinge assembly of FIG. 8.
Figure 13:
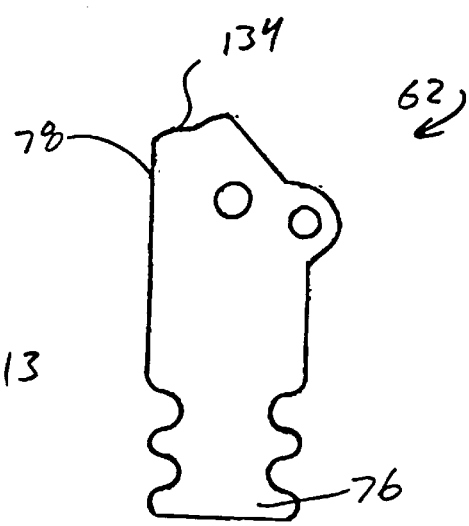
FIG. 13 is a front view of the lower arm of the hinge assembly of FIG. 8.

With particular reference to FIGS. 1 and 4, the calf cuff component 16 is constructed to include a calf transverse portion 44 which circumscribes the anterior portion of the wearer's leg 12 below the knee. The calf cuff component 16 is shown to further include a lower stabilizing portion or proprioceptive arm 46 connected to the tibial transverse portion 44 through an intermediate segment or keel 48. The keel 48 is positioned to be located on the medial side of the tibia. A center of the transverse portion 44 includes a shallow channel 39 to provide additional clearance from the crest of the tibia. In this manner, a more aggressive purchase of the tibia can be comfortably made so as to better control the tibia. As with the thigh cuff component 14, the calf cuff component 16 is open at the posterior so that it may be placed over the user's leg 12 from the front.

The angled brackets 34 are preferably constructed of thin steel or other suitable material. For point of reference, the stem of each of the cushioning members 36 define an axis. The angled brackets 34 are configured to permit movement of the associated cushioning member 36 along this axis during flexion and extension of the knee. This movement in cooperation with the elastic strap 38 functions to maintain a clamping force against the wearer's leg 12 in an area above the knee to a comfortable yet effective degree and thereby prevent migration of the brace assembly 10.

Both the thigh and calf cuff components 14 and 16 are made of a lightweight, thermoset or thermoplastic material which can be formed to fit the contours of an individual wearer's leg. One suitable material for forming the cuff components 14 and 16 is a carbon fiber, preimpregnated material with a core material such as balsa wood or an expanding foam adhesive. However, those skilled in the art will readily appreciate that other materials may be employed.

The thigh cuff component 14 and the calf cuff component 16 are padded on the inside by padded bands 50 and 52 which are elastically stretchable and wrap around the wearer's leg both above and below the knee. The padded bands 50 and 52 are suitably secured to the femoral and calf components 14 and 16, respectively, and each include a hooked material portion 53 for attachment anywhere along the respective band 50 or 52. The padded band 50 for the thigh component 14 is shown most particularly in FIG. 10 and is configured to provide a protective barrier between the wearer's leg 12 and the each of the downwardly extending portions 20 and 24 and the transverse member 26. The padded band 50 is further configured to wrap around the wearer's thigh.

The padded band 52 is similarly configured to provide a protective barrier between the wearer's leg 12 and the transverse portion 44, the preprioceptive arm 46 and the keel 48 and to also wrap around the wearer's calf. In the embodiment illustrated, the padded band 52 includes an upper radiused portion 55 or preprioceptive portion 55 that surrounds an anterior portion of the superior calf. The padded bands 50 and 52 may be secured to the associated one of the thigh and calf components 14 and 16 with looped material, with fasteners, or in any other known manner.

The brace assembly 10 may be further secured to the wearer's leg 12 through a pair of non-elastic straps 56 (shown in FIG. 1). In the preferred embodiment, the straps 56 are secured to the assembly 10 through a plurality of hook assemblies 58. One of the hook assemblies 58 will be described with particular reference to FIGS. 7A through 7C. The hook assemblies 58 are shown to include a cap member or base 55 that is received within one of a plurality of countersunk portions 57 of the thigh and calf components 14 and 16. A rear surface of the base 55 includes an internally threaded boss portion 59. The boss portion 59 receives a threaded fastener 61 which passes through a washer and an aperture (not particularly shown) in the associated one of the thigh and calf components 14 and 16. The base 55 includes a pair of cut-out portions 63 which preferably taper in a radially inward direction. The cut-out portions 63 receive free ends of a wire form or hook proper 65.

The hook proper 65 is configured such that when the hook assembly 58 is secured to the assembly 10, the hook proper 65 outwardly extends due to an inherent spring bias. As such, the hook propers 65 are more easily engaged by the straps 56. Upon tightening, the straps 56 draw the hook propers 65 against the associate base 55.

In the embodiment illustrated, a lower one of the straps 56 starts at the hook assembly 58 of a medial distal end of the preprioceptive arm 46, passes through the hook assembly 58 positioned at the lateral proximal side of the transverse portion 44 and terminates at the hook assembly 58 located at the medial proximal side of the transverse portion 44. An upper one of the straps 56 starts at the hook assembly 58 positioned at the corner 28, passes through the hook assembly 58 positioned on medial proximal one of the downwardly extending portions 20 and terminates at the hook assembly 58 positioned on the lateral distal one of the hook assembly 58 positioned on the medial one of the downwardly extending portions 24. Preferably, the straps 56 secure to themselves through hook and loop material portions (not shown).

A medial one of the hinge assemblies 18 of the orthopaedic brace assembly 10 of the present invention is shown in further detail in the exploded view of FIG. 8. It will be understood that the lateral one of the hinge assemblies 18 is a substantial mirror image thereof. The hinge assemblies 18 provide for an articulating connection between the thigh component 14 and the calf component 16.

The hinge assembly 18 is preferably illustrated as a four bar linkage hinge assembly with polycentric motion and is shown to generally include a first or upper arm 60, a second or lower arm 62, a first or outer link 64 and a second or inner link 66. In one application, the upper arm 60, the lower arm 62, the outer link 64, and the inner link 66 are each constructed of a lightweight material such as aluminum, stainless steel, titanium, or other suitable material. However, those skilled in the art will appreciate that alternate materials having suitable strength requirements may be readily substituted in the teachings of the present invention.

The upper arm 60 includes an upper end 68 which is secured to the downwardly extending portion 24. A lower end 70 of the upper arm 60 is secured to both the outer link 64 and the inner link 66 for relative pivotal motion. A first pin 72 defines a pivot axis between the upper arm 60 and the outer link 64. A second pin 74 defines a pivot axis between the upper arm 60 and the inner link 66.

The lower arm 62 is similarly constructed to include a lower end 76 attached to the calf cuff component 16 and an upper end 78 pivotally connected to both the inner and outer links 66 and 64. A first pivot pin 80 pivotally interconnects the lower arm 62 and the outer link 64 and a second pivot pin 82 pivotally interconnects the tibial arm 76 and the inner link 66. In the application illustrated, the first pin 80 defines the pivot axis between the tibial arm 76 and the outer link 64 and is fixedly carried by the outer link 64 and rotatably attached to the lower arm 62. The second pivot pin 82 defines the pivot axis between the lower arm 62 and the inner link 66 and is fixedly carried by the inner link 66 and pivotally interconnected to the lower arm 62.

The hinge assemblies 18 include a condyle pad 86 for placement adjacent the wearer's leg 12. The condyle pads 86 serve as protective members against impacts in the lateral and medial directions of the wearer's leg 12. One of the condyle pads 86 is shown most particularly in FIG. 8.

In the embodiment of FIG. 8, the condyle pads 86 are shown to include a cushioning portion 88 and a mounting portion 90. In one application, the cushioning portion 88 carries a hook material for releasable attachment to a looped material carried by the mounting portion 90. The mounting portion 90 is captured between the outer link 66 and the upper and lower arms 60 and 62.

Figure 14:
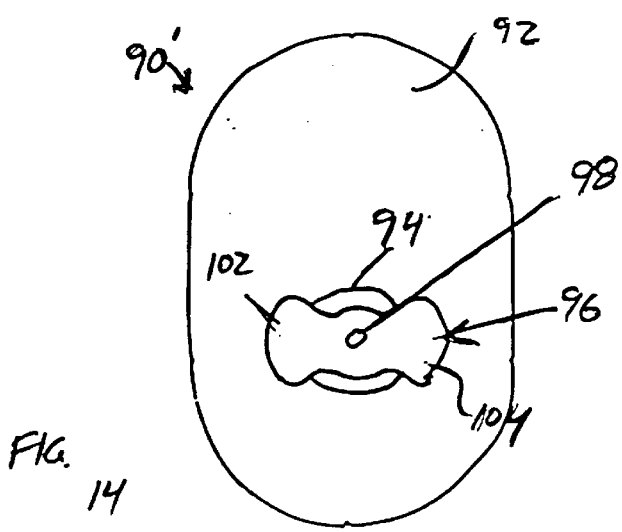
FIG. 14 is a plan view of a mounting portion for releasable attachment to the inner link of FIG. 9.
Figure 10:
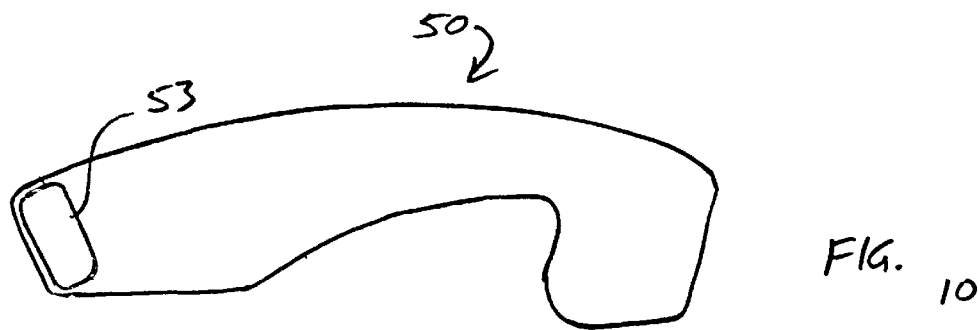
FIG. 10 is a front view of a thigh band of the orthopaedic brace assembly of the present invention.
Figure 11:
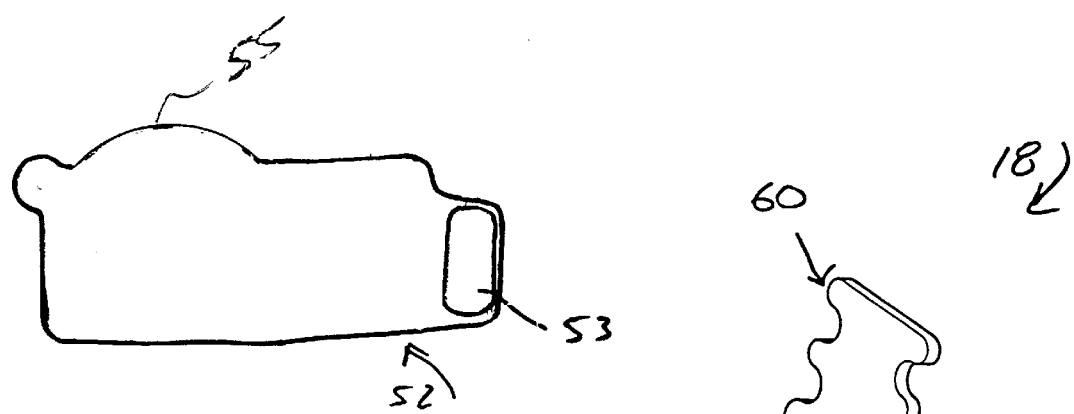
FIG. 11 is a front view of a calf band of the orthopaedic brace assembly of the present invention.
Figure 9:
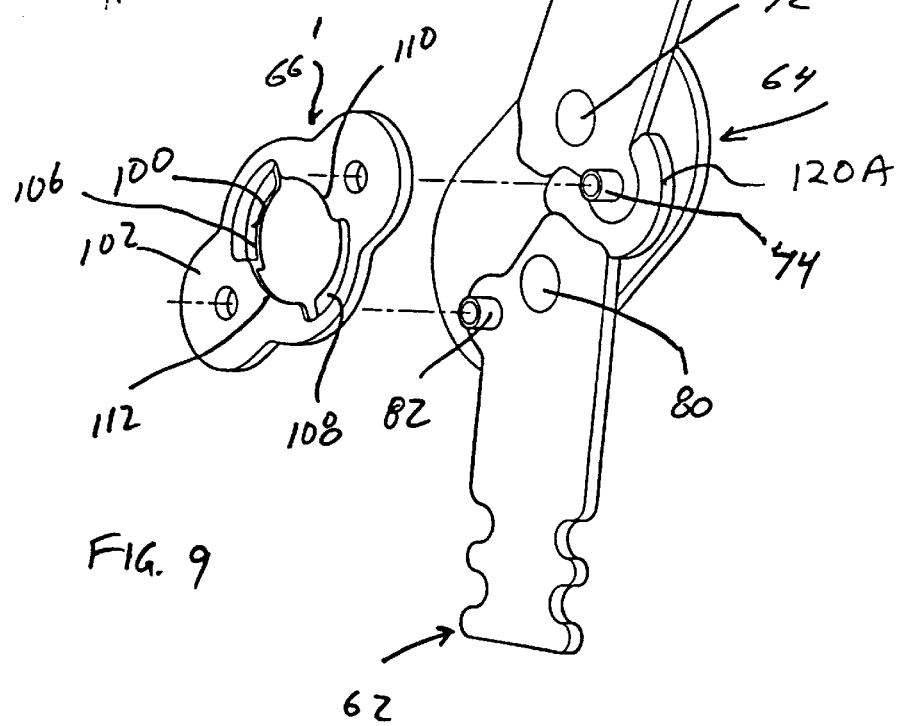
FIG. 9 is a partially exploded perspective view of the hinge assembly of FIG. 8, illustrated to include an alternate inner link and operatively associated with a removable stop.

In the embodiment of FIG. 9, an alternate inner link 66' is shown which cooperates with an alternate mounting portion 90' (shown most particularly in FIG. 14). With this arrangement, the mounting portion 90' is adapted to be quickly and easily secured to the remainder of the hinge assembly 18. In the embodiment illustrated, the mounting portion 90' is again secured to the inner link 66' of the hinge assembly 18. In this manner, the condyle pad 86 moves with the inner link 66 throughout the range of articulation of the wearer's knee.

As shown in FIG. 14, an outer facing side 92 of the mounting member 90 is formed to include a circular boss 94 to which a retaining element 96 is fixedly secured by a rivet 98. The retaining element 96 is shown to have a generally bow-tie shape. The element 96 is received in a similarly shaped recess 100 (shown particularly in FIG. 9) defined in a inner facing side 102 of the inner link 66. Upon insertion, opposing ends 102 and 104 of the element 96 are positioned against flanges 106 and 108, respectively. The mounting member 90' is then rotated clockwise (as shown in FIG. 9) approximately 30 to 35 degrees such that the ends 102 and 104 are positioned below a pair of flanges 110 and 112, respectively.

With additional reference to FIGS. 15–22, both of the hinge assemblies 18 of the present invention is shown to include a series of stops 120A–120F for selectively limiting the range of articulation of the wearer's knee. In the embodiment illustrated, the stops 120A–120F are employed to limit the degree of extension of the wearer's knee. Alternatively, the stops may be configured to selectively limit flexion of the knee or both extension and flexion.

FIGS. 15–22 illustrate the stops 120A–120F operatively associated with the hinge assembly 18 to include the alternate inner link 66' of FIG. 9. The stops 120A–120F will be understood to be identically employed with the inner link 66 of the arrangement shown in FIG. 8.

Figure 15:
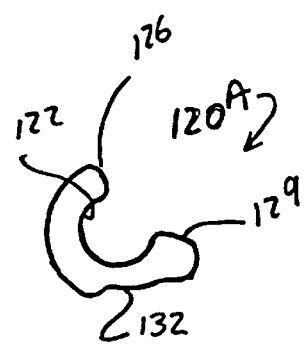
FIG. 15 is a front view of the removable stop of FIG. 9.
Figure 17:
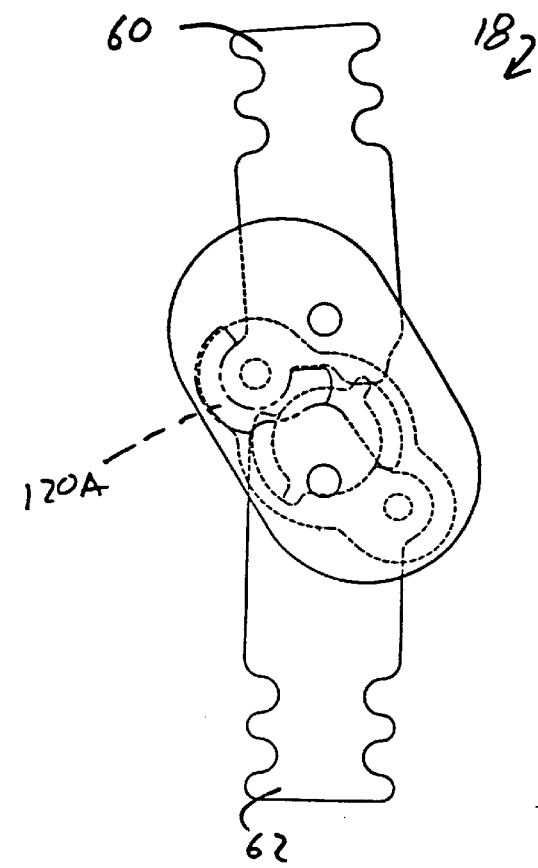
Figure 16:
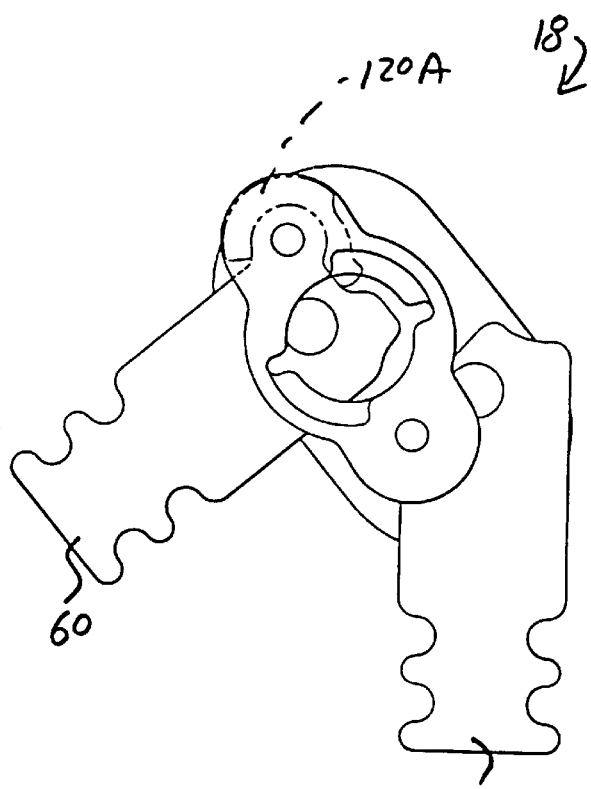
FIG. 16 is a rear view of the hinge assembly of FIG. 4 illustrated articulated to degree substantially consistent with a fully contracted knee position.
Figure 18:
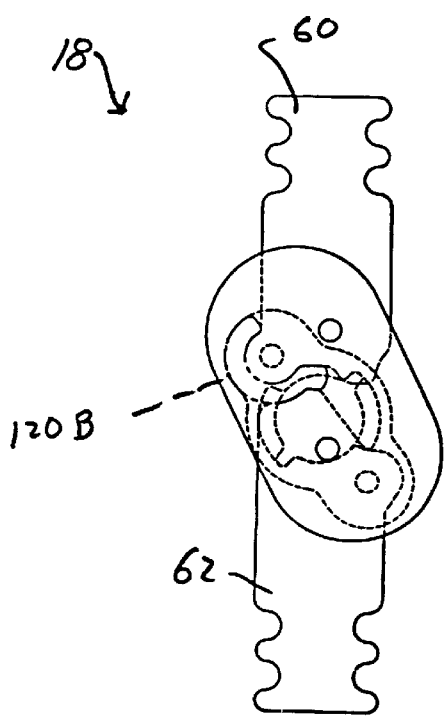

A first stop 120A of the series of stops is shown in FIGS. 15–17. The first stop 120A is intended to limit extension of the wearer's knee to −10° from longitudinal axially alignment of the wearer's femur and tibia as viewed from a medial or lateral side. In particular and in accordance with the preferred embodiment of the present invention, the series of stops is shown to include five additional stops 120B, 120C, 120D, 120E, and 120F for establishing maximum extension angles of 0°, 10°, 20°, 30°, 40°, respectively (from longitudinal axial alignment of the tibia and femur). Each of the stops 120A–120F is configured to quickly and easily engaged the remainder of the hinge assembly 18 without the need for discrete tools. In one application, the stops 120A–120F are each injection molded of a resilient plastic or glass reinforced nylon.

The first stop 120A is illustrated particularly in FIG. 15 to define a partial cylindrical opening 122. The opening 122 corresponds in size and shape to a generally cylindrical extension 124 carried at the lower end 70 of the upper arm 60. The circular opening 122 preferably defines slightly more than half of a circle. Due to the resilient nature of the stop 120A, the circular opening 122 snapingly engages the circular extension 124. A first end 126 of the stop 120A abuts one of the vertical sides 128 of the upper arm 60 and a second end 129 abuts a lower side 130 of the femoral arm. In this manner, rotation of the stop 120A relative to the upper arm 60 is prevented upon the snapping engagement. The stop 120 is also captured in a medial lateral direction between the inner link 66' and the outer link 64.

The stop 120A is configured to include a lower stop surface 132 configured to matingly abut an upper side 134 of the lower arm 62. Specifically, the lower stop surface 132 engages the upper side 134 at the point of desired maximum extension of the wearer's knee. For the first stop 120A, this point of maximum desired extension is −10°. As shown particularly in FIG. 16, the series of stops of the present invention will not limit articulation of the hinge assembly 18 in flexion.

The remaining stops 120B–120F are shown in FIGS. 18–22 operatively associated with the remainder of the hinge assembly 18. It will be understood that these remaining stops 120B–120F are substantially identical to the first stop 120A with the exception that the lower stop surface 132 is configured and positioned relative to the circular opening 122 so as to engage the upper surface 134 of the lower arm 62 at the desired maximum angle of extension.

While the invention has been described in the specification and illustrated in the drawings with reference to a preferred embodiment, it will be understood by those skilled in the art that various changes may be made and equivalents may be substituted for elements thereof without departing from the scope of the invention as defined in the claims. In addition, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the description of the appended claims. For example, various aspects of the teachings of the present invention are applicable for bracing other hinged joints, such as an elbow.

What is claimed is:

1. An orthopaedic brace assembly for constraining movement of a knee of a wearer's leg, the orthopaedic brace assembly comprising:
   a thigh cuff component for engaging the wearer's leg above the knee, the thigh cuff component including a suspension assembly having a pair of cantilevered arms for engaging the wearer's leg;
   an elastic strap connecting the pair of cantilevered arms;
   a calf cuff component for engaging the wearer's leg below the knee; and
   a pair of hinge assemblies coupling the thigh cuff component and the calf cuff component for relative articulation.

2. The orthopaedic brace assembly of claim 1, wherein each of the pair of cantilevered arms includes a partially spherical and removable padded portion for directly engaging the wearer's leg.

3. The orthopaedic brace assembly of claim 1, wherein the calf cuff component includes first and second arcuate portions for anteriorly circumscribing at least a portion of the wearer's leg below the knee, the first and second arcuate portions interconnected by an intermediate member extending vertically therebetween, the second arcuate portion disposed generally perpendicular to the intermediate member and cantilevered from the intermediate member such that the second arcuate portion has a free end.

4. The orthopaedic brace assembly of claim 1, wherein each hinge assembly includes a first arm, a second arm, a first link and second link for interconnecting the first and second arms for relative movement to one another through a range of articulation, the first link pivotally interconnected to the first arm and the second arm, the second link pivotally interconnected to the first arm and the second arm, and a removable stop member for adjusting a range of articulation, the removable stop member secured to the first arm of the associated hinge assembly.

5. A polycentric hinge assembly for pivotally connecting first and second cuff components of an orthopaedic brace, the hinge assembly comprising:
   a first arm for fixed attachment to the first cuff component;
   a second arm for attachment to the second cuff component;
   a first link and a second link for interconnecting the first and second arms for relative movement to one another through a range of articulation, the first link pivotally interconnected to the first arm and the second arm, the second link pivotally interconnected to the first arm and the second arm; and
   a series of stops which selectively snap fit directly to the first arm for articulation with the first arm, the series of stops for limiting the range of articulation of the hinge assembly.

6. The hinge assembly for an orthopaedic brace of claim 5, wherein each stop defines a generally circular opening releasably receiving a generally circular extension of the first arm.

7. The hinge assembly for an orthopaedic brace of claim 6, wherein the second arm includes a stop surface for engaging a selected one of the series of stops.

8. The hinge assembly for an orthopaedic brace of claim 6, further comprising a condylar pad releasably attached to the first link for movement with the first link.

9. The hinge assembly for an orthopaedic brace of claim 8, where in the condylar pad includes a mounting portion having a mounting element received by the first link.

10. A hinge assembly for pivotally connecting first and second cuff components of an orthopaedic brace, the hinge assembly comprising:

a first arm for attachment to the first cuff component;

a second arm for attachment to the second cuff component;

a first link and a second link for interconnecting the first and second arms for relative movement to one another through a range of articulation, the first link pivotally interconnected to the first arm and the second arm, the second link pivotally interconnected to the first arm and the second arm; and at least one removable stop directly attached direct to the first arm for articulation with the first arm, the at least one stop for limiting the range of articulation of the hinge assembly.

11. The hinge assembly for an orthopaedic brace of claim 10, wherein the stop is snap fit to the first arm.

12. The hinge assembly for an orthopaedic brace of claim 10, wherein the at least one stop includes a plurality of stops, the stops of the plurality of stops being selectively attached to the first arm.

13. The hinge assembly for an orthopaedic brace of claim 10, wherein the hinge assembly is a polycentric hinge assembly.

14. The hinge assembly for an orthopaedic brace of claim 10, wherein the stop at least partially defines a generally cylindrical opening releasably receiving a generally circular extension of the first arm.

15. The hinge assembly for an orthopaedic brace of claim 10, wherein the second arm defines a stop surface for engaging the stop to limit the range of articulation of the hinge assembly.

16. The hinge assembly for an orthopaedic brace of claim 10, in combination with the first and second cuff components, the first arm having a first end connected to the first cuff component and a second end receiving the stop, the second arm having a first end attached to the second cuff component and a second end defining the stop surface.

17. The hinge assembly for an orthopaedic brace of claim 10, further comprising a condylar pad releasably attached to the first link for movement with the first link.

18. The hinge assembly for an orthopaedic brace of claim 17, wherein the condylar pad includes a mounting portion having a mounting element received by the first link.

\* \* \* \* \*